United States Patent
Sugianto

(10) Patent No.: US 9,480,803 B2
(45) Date of Patent: *Nov. 1, 2016

(54) DOSE COUNTER WITH LOCKOUT MECHANISM

(71) Applicant: MAP PHARMACEUTICALS, INC., Irvine, CA (US)

(72) Inventor: Alfred Sugianto, Menlo Park, CA (US)

(73) Assignee: MAP Pharmaceuticals, Inc., Irvine, CA (US)

(*) Notice: Subject to any disclaimer, the term of this patent is extended or adjusted under 35 U.S.C. 154(b) by 224 days.

This patent is subject to a terminal disclaimer.

(21) Appl. No.: 14/155,581

(22) Filed: Jan. 15, 2014

(65) Prior Publication Data

US 2014/0123975 A1 May 8, 2014

Related U.S. Application Data

(63) Continuation of application No. 12/387,867, filed on May 7, 2009.

(60) Provisional application No. 61/126,855, filed on May 7, 2008.

(51) Int. Cl.
- *A61M 11/00* (2006.01)
- *A61M 15/00* (2006.01)
- *A61M 11/04* (2006.01)

(52) U.S. Cl.
CPC .......... *A61M 15/0065* (2013.01); *A61M 11/04* (2013.01); *A61M 15/009* (2013.01); *A61M 15/0026* (2014.02); *A61M 15/0076* (2014.02); *A61M 15/0081* (2014.02); *A61M 15/0091* (2013.01)

(58) Field of Classification Search
CPC ......... A61M 15/0081; A61M 15/009; A61M 15/0091; A61M 11/04; A61M 15/0026; A61M 15/0065; A61M 15/0076
See application file for complete search history.

(56) References Cited

U.S. PATENT DOCUMENTS

| | | | |
|---|---|---|---|
| 5,119,806 A | 6/1992 | Palson et al. | |
| 8,720,433 B2 * | 5/2014 | Sugianto | A61M 15/009 128/200.14 |
| 2002/0078950 A1 | 6/2002 | O'Leary | |

(Continued)

FOREIGN PATENT DOCUMENTS

| | | |
|---|---|---|
| WO | 94/04209 A1 | 3/1994 |
| WO | 01/34231 A1 | 5/2001 |

(Continued)

OTHER PUBLICATIONS

International Preliminary Report on Patentability mailed on Nov. 9, 2010, for PCT Patent Application No, PCT/US09/02860, filed on May 7, 2009, five pages.

(Continued)

*Primary Examiner* — Peter S Vasat
(74) *Attorney, Agent, or Firm* — Barbara C. Potts

(57) ABSTRACT

A medicament dispenser, in particular a metered dose inhaler, which is able to count the number of time the dispenser is activated and then disable the device, which then prevents any additional medicament from being dispensed. Additional embodiments include a medicament dispenser which are adapted to display either the number of activations that have occurred or the number of activations remaining.

8 Claims, 20 Drawing Sheets

(56) References Cited

U.S. PATENT DOCUMENTS

| | | |
|---|---|---|
| 2002/0189611 A1 | 12/2002 | Greenwood et al. |
| 2006/0231093 A1* | 10/2006 | Burge ............... A61M 15/0068 128/203.15 |
| 2006/0283444 A1 | 12/2006 | Jones et al. |
| 2007/0062518 A1* | 3/2007 | Geser ............... A61M 15/0065 128/200.14 |

FOREIGN PATENT DOCUMENTS

| | | |
|---|---|---|
| WO | 2004/041339 A2 | 5/2004 |
| WO | 2005/041850 | 5/2005 |
| WO | 2005/079727 | 9/2005 |
| WO | 2007/124406 | 11/2007 |

OTHER PUBLICATIONS

International Search Report mailed on Jun. 23, 2009, for PCT Patent Application No. PCT/US09/02860, filed on May 7, 2009, two pages.

Written Opinion mailed on Jun. 23, 2009, for PCT Application No. PCT/US09/02860, filed on May 7, 2009, four pages.

Reply under 37 C.F.R. § 1.111, U.S. Appl. No. 12/387,867 dated Jul. 26, 2012, U.S. Pat. No. 8,720,433 Prosecution History, pp. 21.

\* cited by examiner ured number of doses. For standard pills or tablets, only
DOSE COUNTER WITH LOCKOUT MECHANISM This application is a continuation of U.S. patent application Ser. No. 12/387,867, filed May 7, 2009 which claims priority under 35 U.S.C. §119(e) from U.S. Provisional Application Ser. No. 61/126,855, filed May 7, 2008, which are hereby incorporated by reference in their entirety.

FIELD OF THE INVENTION

The present invention described herein relates to the field of drug delivery. More specifically, the present invention relates to an inhaler and a method for delivering doses of aerosolized medication for inhalation by a patient into the lungs which incorporates a dose counter component having a lockout feature and a method for counting the number of drug doses in an inhaler and inactivating the inhaler, so that no more drug can be delivered, when a predetermined number of doses have been delivered.

BACKGROUND OF THE INVENTION

Aerosols are increasingly being used for delivering medication for therapeutic treatment of the lungs as well as systemic delivery of therapeutic agents. For example, in the treatment of asthma, inhalers are commonly used for delivering bronchodilators such as $\beta_2$ agonists and anti-inflammatory agents such as corticosteroids. Two types of inhalers are in common use, pressurized metered dose inhalers (pMDIs) and dry powder inhalers (DPIs). Both types of inhalers have as their object the delivery of medication (which is typically in the form of a solid particulate or powder) into the airways of the lungs at the location of the condition being treated or for systemic delivery.

In a traditional pMDI device, the medication is provided in a pressurized aerosol canister, with the medication being suspended or dissolved in a liquid propellant such as a chlorofluorocarbon (CFC) or hydrofluoroalkane (HFA). The canister includes a metering valve having a hollow discharge stem which can be depressed inward against an internal spring. Once the discharge stem is fully depressed into the canister a metered volume of propellant-medication mixture is discharged through the stem. The discharge is in the form of an aerosol comprising fine droplets of propellant in which particles of the medication are suspended or dissolved. A typical pMDI for use with such a canister includes a housing having an actuator and a nozzle. The canister is inserted into the housing with the hollow discharge stem of the canister being received in a bore in the actuator. Depressing the closed end of the canister causes the stem to be pushed inward into the canister so that a metered volume of medication is discharged through the nozzle. The housing further defines a flowpath in fluid communication with the nozzle, with the flowpath having an outlet at a mouthpiece portion of the housing, such that the aerosolized medication may be inhaled after it exits the mouthpiece portion. The patient either inserts the mouthpiece into the mouth with the lips closed around the mouthpiece, or holds the mouthpiece at a slight distance away from an open mouth. The patient then depresses the canister to discharge the medication, and simultaneously inhales.

In the field of inhalers, it is known to use a dose counter for tracking and/or displaying the number of doses that have been dispensed or that remain to be dispensed from the inhaler. Such conventional counters are generally incremented each time a drug dose is expelled by the inhaler.

In addition, there exists a need to inactivate the inhaler in order to prevent a patient from delivering more than the required number of doses. For standard pills or tablets, only the actual number of doses prescribed by the physician are dispensed by the pharmacist. For an inhaler the problem is far more complicated. It isn't practical to limit the number of doses by limiting the amount of propellant/drug in the canister because then the last few actuations of the inhaler would only deliver a partial dose. Thus there is a need to be able to inactivate the inhaler while there is still sufficient content in the canister to provide for the full amount of drug delivery for each of the actuations of the inhaler.

In addition it may be difficult from a manufacturing perspective to properly fill the canister with a de minimus amount of medicament. Thus from a quality control perspective, it is better to fill the canister with an amount that permits reproducible filling and then limit the number of doses by use of the counter/lockout mechanism of the present invention.

The disclosed invention was developed to correct the above-described problem. The disclosed invention of a dose counter/lockout mechanism is shown incorporated into an inhaler having a pMDI medication canister, a synchronized breath-actuated trigger, and a flow control chamber. However, the disclosed dose counter/lockout mechanism could be incorporated into a inhaler in which the canister actuation is done manually.

Furthermore, the disclosed inhaler includes a dose counter that increments only after an actual delivery of drug from the medication canister as occurs when the canister is depressed beyond a certain point. Upon reaching a predetermined number of actuations two things occur. One is that the dose counting wheel can no longer be incremented. Secondly, a spring assembly, which needs to be cocked (i.e. compressed) in order to depress and therefore discharge medicament from the canister, is disengaged from the rest of mechanism and therefore can't be compressed and therefore can't cause the medicament canister deliver a dose.

BRIEF SUMMARY OF THE INVENTION

The present invention described herein involves an actuation counter/lockout mechanism which disables a device after a predetermined number of mechanical actuations have occurred. Though described herein as being a component of a pressurized metered dose inhaler, the invention could be a component in any type of mechanical device which can cause a movable carriage to be translated. For example, the device might be used in conjunction with a device which delivers sugar pills to experimental lab animals and would be deactivated after the animal has triggered the device a predetermined number of times. The following descriptions, discussions and drawings will be directed to the invention being incorporated into a specific class of device—that of a pMDI. However, it will be understood by one skilled in the art that this is only one of many possible types of mechanical devices that could incorporate the invention.

The present invention also includes a method for counting and displaying the number of actuation cycles of a pMDI. Furthermore, the method may include a deactivation step which prevents the inhaler from being able to actuate the pMDI canister.

The foregoing and other features and advantages of the invention are apparent from the following detailed description of exemplary embodiments, read in conjunction with the accompanying drawings. The detailed description and the drawings are merely illustrative of the invention rather than limiting the scope of the invention.

BRIEF DESCRIPTION OF THE DRAWINGS

The foregoing summary, as well as the following detailed description of preferred embodiments of the invention, will be understood when read in conjunction with the appended drawings. For the purpose of illustrating the invention, there is shown in the drawings embodiments which are presently preferred. It should be understood, however, that the invention is not limited to the precise arrangements and configurations shown.

I. DIAGRAMMATIC DEPICTION OF THE DOSAGE COUNTER-LOCKOUT

The diagrams shown in FIGS. 1A-1H are meant to provide a general functional explanation of how the dosage counter/lockout features works. Initially a description of the general operation of an inhaler without the dosage counter/lockout mechanism is shown in FIGS. 1A-1D and described below. The reference numbers below for FIGS. 1A-1H, do not match the reference numbers used in FIGS. 2-18.

Figure 1A:
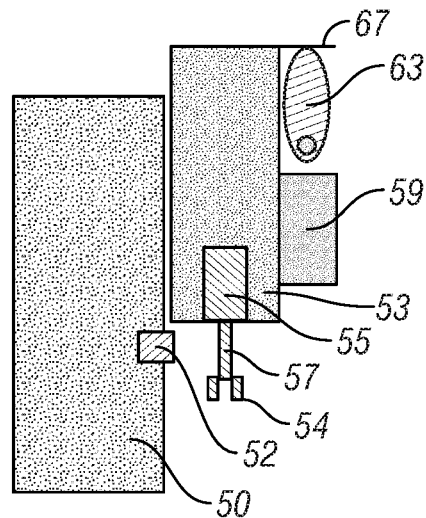
FIGS. 1A-1D depict in diagrammatic form the general operation of a prior art inhaler.

FIG. 1A: Cradle 53 holds the Canister 55 which has projecting from the canister, a hollow spring loaded Canister Stem 57. Canister 55 is pressurized with a propellant containing a medicament, usually as a solution or a particulate suspension. When Canister Stem 57 is depressed and pushed against the spring pressure into the body of Canister 55, a measured aliquot of the canister contents are expelled under pressure of the propellant out of the hollow Canister Stem 57 and into the inspired airflow caused by the patient breathing in through the Inhaler Body 50.

Cradle 53 is rigidly attached to Spring Assembly 59. Cradle 53 is slideably attached to Inhaler 50 but limited in its downward direction via Cradle Latch 52. Cradle Latch 52 can be deactivated by various means which then allows Cradle 53 to slideably move along Inhaler Body 50. Cradle Latch 52 can be designed to uncouple in response to air flow through the Inhaler 50 caused by a patient breathing in through the Inhaler Body 50. Instead of being breath actuated, Cradle Latch 52 can alternatively be designed to be activated manually which means the patient must coordinate the inspiration of a breath with the manual activation of Cradle Latch 52.

FIG. 1A depicts what is considered to be the Reset or Resting configuration. Cam 63 is pushing against Reset Arm 67 which is holding Cradle 53 and Spring Assembly 61 in the fully upward position such that Cradle Latch 52 can be positioned in the engaged position.

Figure 1B:
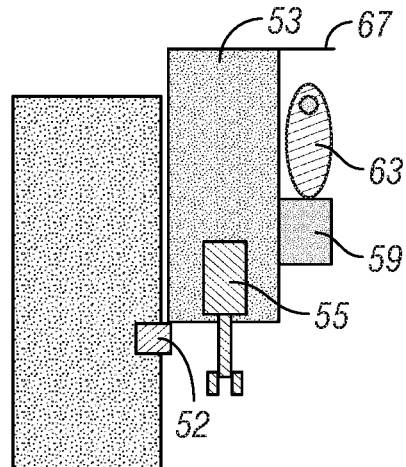

In FIG. 1B, Cam 63 has rotated such that it is now pushing on Spring Assembly 59. And because Spring Assembly 59 is fixedly attached to Cradle 53, Cradle 53 is biased slightly downward and is held in place by Cradle Latch 52. Because the Moving Assembly (Spring Assembly 59, Cradle 53, and Canister 55) is held in position, the springs in Spring Assembly 59 are compressed as shown by the box representing Spring Assembly 59 being shown smaller in size.

Figure 1C:
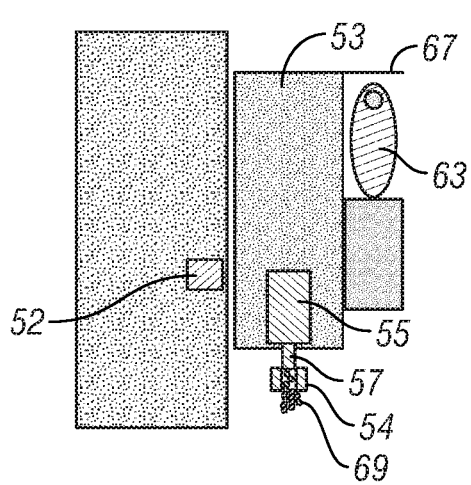

FIG. 1C shows the configuration after a patient has actuated Cradle Latch 52 either manually or by drawing in a breath which causes Cradle Latch 52 to uncouple and allows the Moving Assembly to be biased downwards by the expansion of the compressed springs.

Cradle 53 is configured to bias Canister 55 downwards which forces Canister Stem 57 to be biased against Stem Retainer 54. As a result of being biased against Stem Retainer 54, Canister Stem 57 is displaced into Canister 55, which causes a measured aliquot of medicament to be discharged from the canister as discussed above.

Figure 1D:
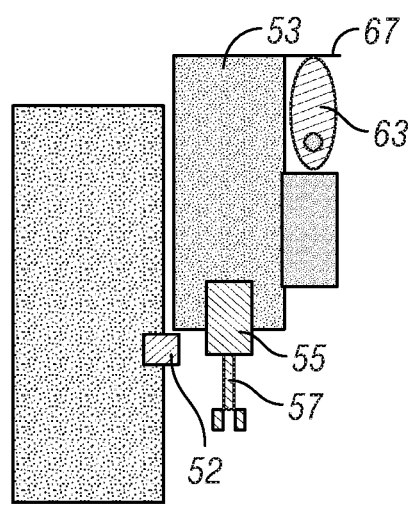

After the dose of Medicament 69 has been discharged, Cam 63 is rotated back to the reset or rest position as shown in FIG. 1D. The lobe on Cam 63 biases Reset Arm 67 upward, which in turn biases Moving Assembly back to its upward position. With the Moving Assembly located in its highest upward location, Cradle Latch 52 is then automatically reset.

Now the device is ready for the next actuation cycle. In practice, Cam 63 is attached to a Cocking Lever which also functions as mouthpiece cover which is positioned in the closed position in FIG. 1A and FIG. 1D (Reset Position) and rotated to the open position in FIG. 1B (cocked position) and FIG. C (discharged position).

When the patient picks up the inhaler, the cover is closed and all components are as shown in FIG. 1A. The patient rotates the cover to the fully open position, which makes the inhaler available for use and which rotates Cam 63 and configures the device as shown in FIG. 1B. With the cover open, the patient draws in a breath, actuates the breath actuated trigger which then allows the medicament to be dispensed into the air stream that is being drawn into the lungs by the patient. During medicament delivery the Inhaler is in the configuration shown in FIG. 1C.

When the inhalation and medicament delivery are finished, the patient rotates the cover closed, which causes Cam 63 to be rotated back to its reset position which places the device in the configuration shown in FIG. 1D, which is in fact the same as FIG. 1A. When Cradle 53 is placed in the upper position, by the rotation of Cam 63, pressure is removed from Canister 55. The Canister Stem is then pushed back out by the action of the compressed spring(s) in Canister 55 which causes Canister 55 to move back to its reset position.

II. DOSAGE COUNTER—DIAGRAMMATIC DEPICTION OF FIRST COMPONENT OF THE INVENTION

The additional inventive components of the dosage counter lock out functions are now discussed, building upon the description given above.

Figure 1E:
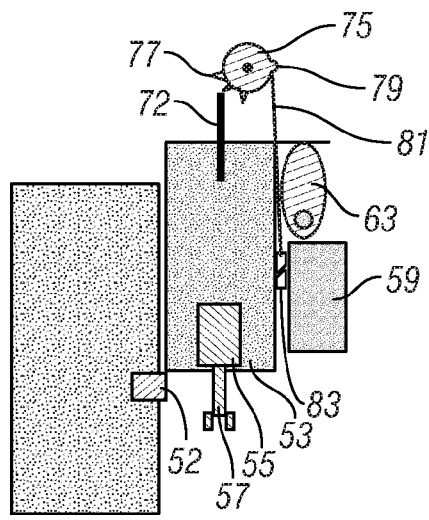
FIGS. 1E-1H depict in diagrammatic form the dosage counter/lockout invention.

As shown in FIG. 1E, there are two additional components needed to effectuate the Dosage Counter feature. A Counter Actuation Arm 72 is attached to Cradle 53. Each time that the Inhaler goes through the resetting function as described above for FIG. 1D, the Counter Actuation Arm 72 pushes against one of a series of Notches 77 on the periphery of the Dosage Counter Wheel 75. On the periphery of the Dosage Counter Wheel is imprinted a series of numbers (usually 1-4 or 1-8). Each time the inhaler goes through the steps of medicament delivery, Counter Actuation Arm causes the Dosages Counter Wheel to rotate a fixed amount which causes the next higher number on the Dosage Counter Wheel to be visible through a window in the housing of the inhaler. The Dosage Counter feature can be designed to either count up or count down as required.

Lock Out

There are two additional features needed to effectuate the lockout function. Notches 77, which are described above, are located along only a portion of the periphery of Counter Wheel 75. The Inhaler is designed to actuate only a predetermined number of times and the number of Notches 77 is same as this predetermined number of actuations. Once the Counter Wheel has advanced this predetermined number of times, there are no more Notches on the wheel that the Contact Arm 72 can contact. Thus Counter Arm 72 has nothing to push against. So even if the Cradle 53 moves back and forth between the positions shown in FIG. 1A and FIG. 1C, because the Contact Arm 72 is not making contact with any Notches 77, the Counter Wheel 75 doesn't rotate.

If no further components were added to the inhaler, the inhaler would still be able to deliver medicament, but the counter wheel would only record a predetermined number of actuations.

There are additional elements needed, which would work in conjunction with the Counter Arm and Counter Wheel, to disable the inhaler. With these additional elements, when the Counter Wheel has been incrementally rotated the predetermined number of times, the inhaler will be disabled and will not deliver medicament. The preferred method of disablement is to prevent the ability of the inhaler to compress the springs. It should be noted that there is no physical blocking or interference of any of the moving parts while in the disabled state and therefore there are no parts put under stress when the inhaler is disabled.

Figure 1F:
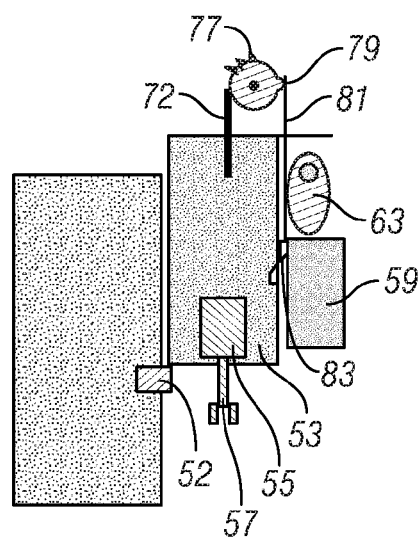

A Dropout Cam 79 is located along the periphery of Counter Wheel 75. When Counter Wheel 75 has been incrementally rotated the proper number of times, it is positioned such that Dropout Cam 79 makes contact with Dropout Tab 81 which causes Spring Latch 83 to disengage as shown in FIG. 1F.

Figure 1G:
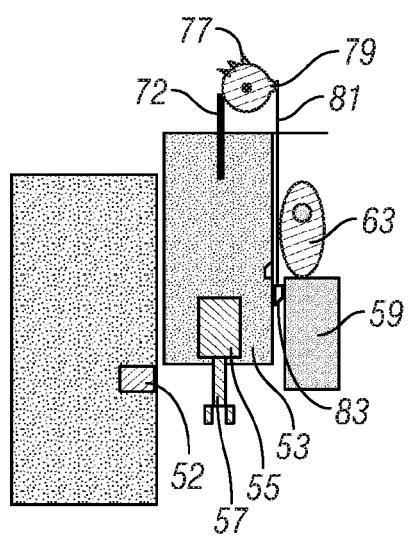
Figure 1H:
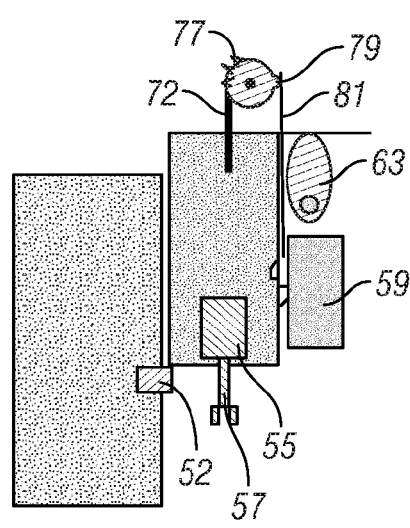

Spring Latch 83, when engaged, rigidly attaches Cradle 53 to Spring Assembly 59. When Dropout Tab 81 is contacted by Dropout Cam 79, it causes the two portions of Spring Latch 83 to separate. Thus Spring Assembly 59 is no longer rigidly attached to Cradle 53. As a consequence, when Cam 63 rotates to the position as shown in FIG. 1G, the springs in Spring Assembly 59 won't compress because the whole Spring Assembly moves in relation to Cradle 53. Therefore there won't be any mechanical force available to bias Cradle 53 and Canister 55 and cause Canister Stem 57 to be depressed into Canister 53 and thus there will be no medicament delivery.

Even if Cradle latch 52 is activated, as shown in FIG. 1G, there is no compressed spring force to drive the Canister. When the Cam 63 is rotated back to its original position, the Moving Assembly is returned to its initial position and Cradle Latch 52 is re-engaged.

Having gone through a diagrammatic depiction of the standard inhaler (FIGS. 1A-1D) and the improved inhaler having a dosage counter and lockout mechanism (FIGS. 1E-1F), a detailed description of the preferred embodiment will now be presented.

DETAILED DESCRIPTION OF THE INVENTION

Figure 2:
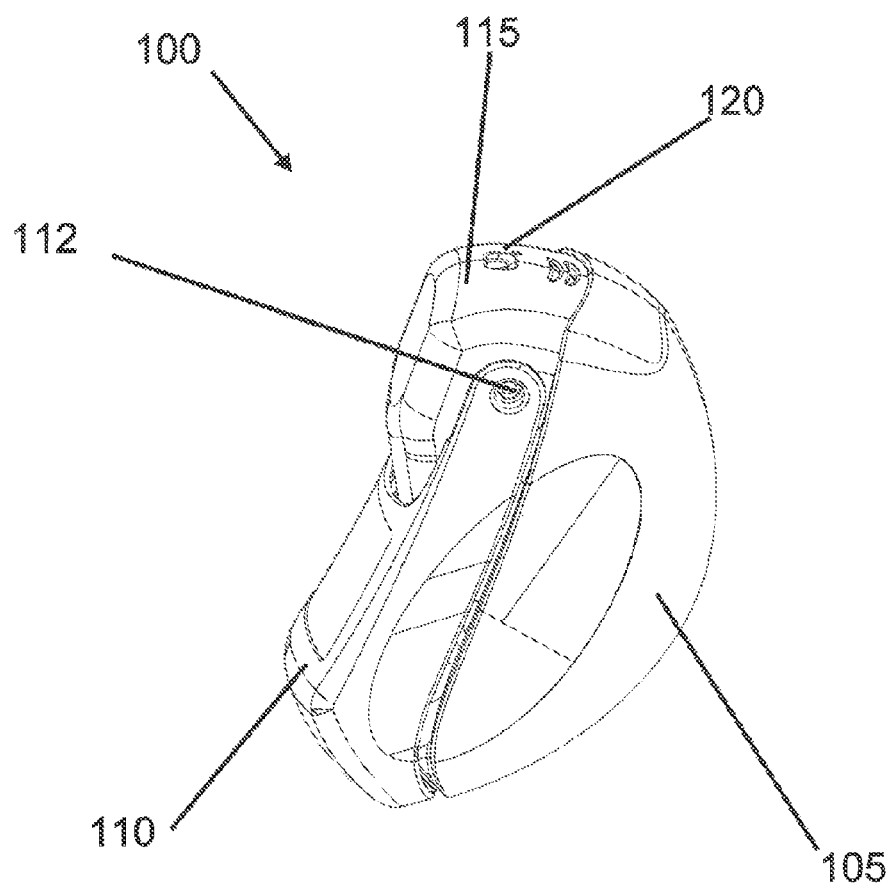
FIG. 2 is an external perspective view of one embodiment of the inhaler.

FIG. 2 shows Inhaler 100 in its closed resting state. Back Cover 105 and Front Cover 115 provide the basic housing structure for Inhaler 100. Cocking Lever 110, attaches to Inhaler 100 and pivots around Pivot Point 112. A Dosage Counter Display Window 120 is formed within Front Cover 115. The actual number of dose that have been delivered is indicated by numbers on a rotating surface that can be viewed through Dosage Counter Display Window 120, as will be discussed in detail below.

Figure 3:
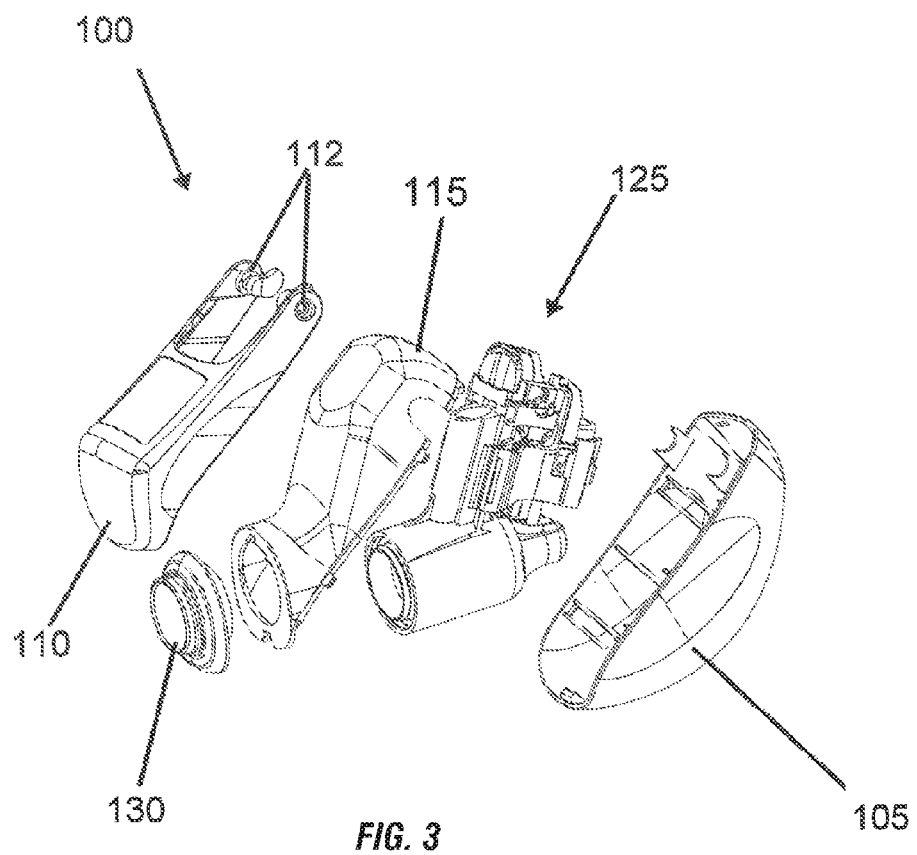
FIG. 3 is another external exploded perspective view of an embodiment of the inhaler.

FIG. 3 is an exploded view of Inhaler 100. Front Cover 115 and Back Cover 105 enclose Manifold Assembly 125. Mouth Piece 130 is inserted through an opening in the bottom of Front Cover 115 and makes a snap fit within an opening in the lower portion of Manifold Assembly 125. Cocking Lever 110, in its closed position, covers Mouth Piece 130. In normal use, Cocking Lever 110 will be manually rotated approximately 135 degrees which fully uncovers Mouthpiece 130 and enabling Mouthpiece 130 to be inserted into the mouth of a patient.

Figure 4:
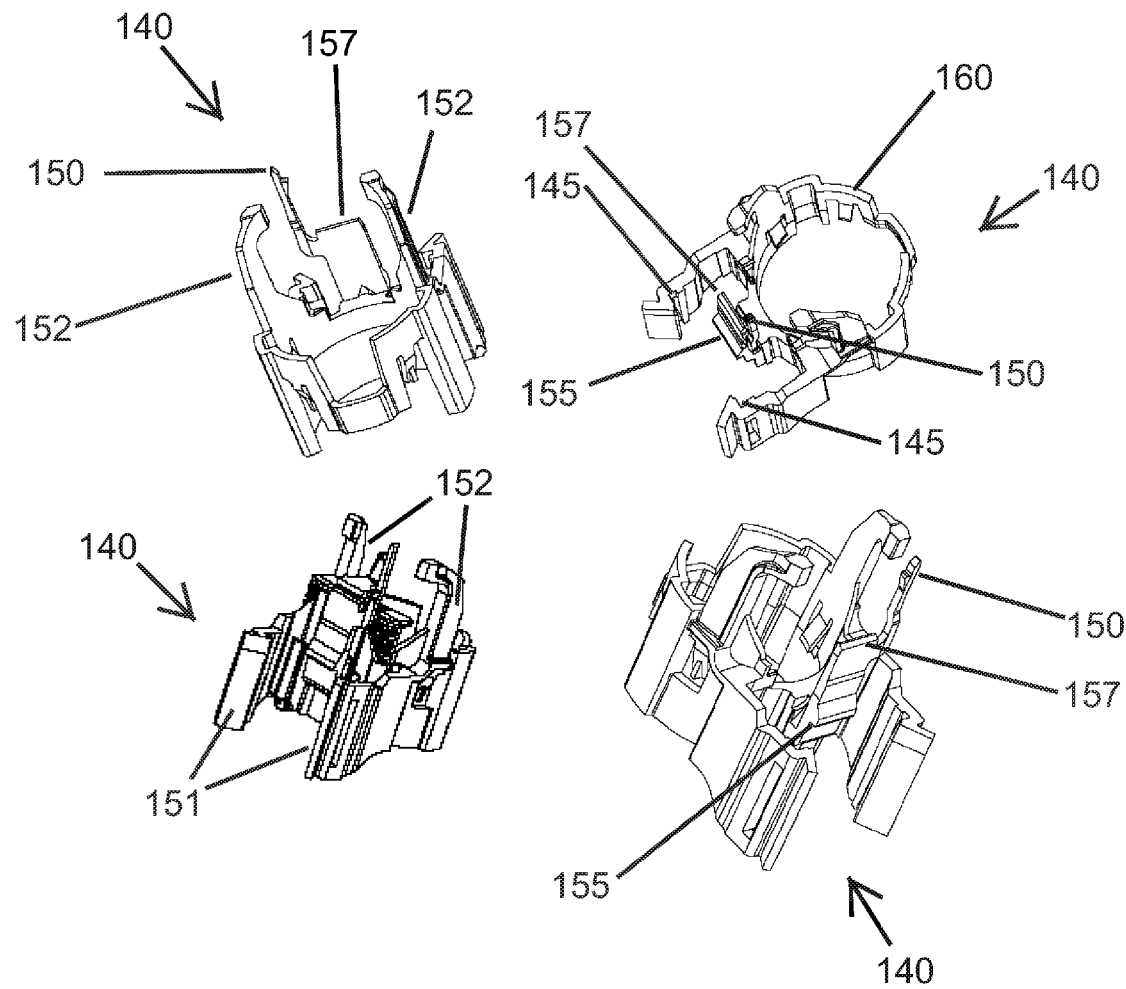
FIG. 4 shows four perspective views of the Cradle of the present invention.
Figure 5A:
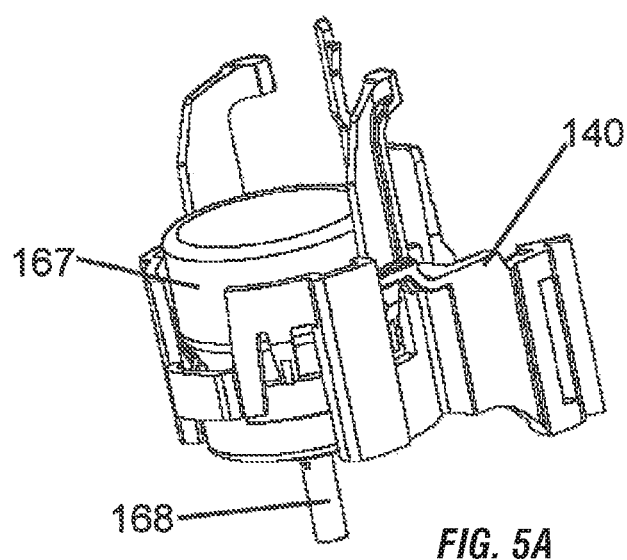
FIG. 5A is a perspective view of a pMDI canister disposed within the Cradle of the present invention.
Figure 5B:
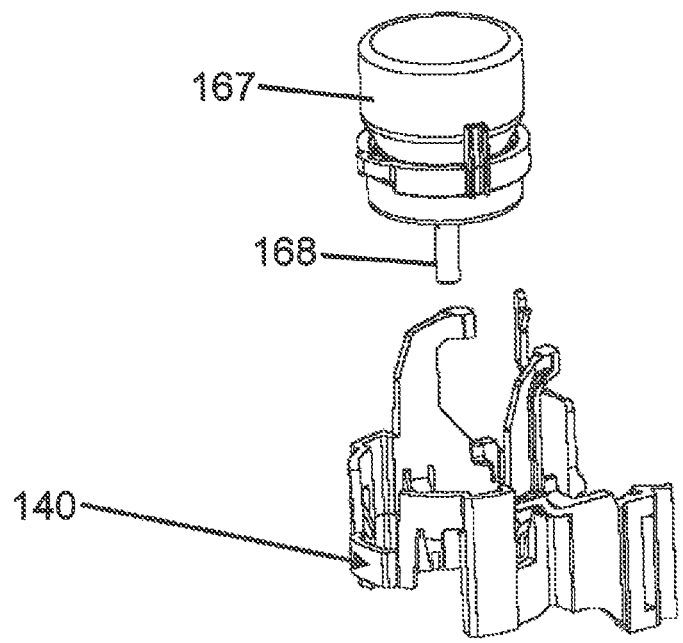
FIG. 5B is an exploded perspective view of the pMDI canister and Cradle shown in FIG. 5A.

FIG. 4 shows Cradle 140 from 4 different views in order that the various components of Cradle 140 can be properly viewed. Cradle 140 has a first pair of arms 151 that extends away from the body of Cradle 140. In the embodiment shown in FIG. 4, Cradle 140 has a second pair of arms (Reset Arms 152) that extends away from the body of Cradle 140. Each of Reset Arms 152 contains a Reset Lobe 290 (see FIG. 17). A clear understanding of all of the functions of the Cradle 140 is critical to an understanding how all of the features of the invention work together. There are six separate functions that the Cradle 140 performs:
 1. Holds the Canister;
 2. Slideably engages the Manifold 170;
 3. Provides one part of the latch to the Manifold;
 4. Provides one part of a latch to the Spring Assembly;
 5. Actuates the Dose Counter Wheel; and
 6. Provides support for the Spring Assembly.
These six functions are now discussed in detail.
 1. Holds the Canister
The Canister 167 is retained within Canister Enclosure 160, which also pushes down on the Canister 167 when the Cradle 140 is pushed down, in order to activate Canister Stem 168 (See FIGS. 5A and 5B).

Figure 6:
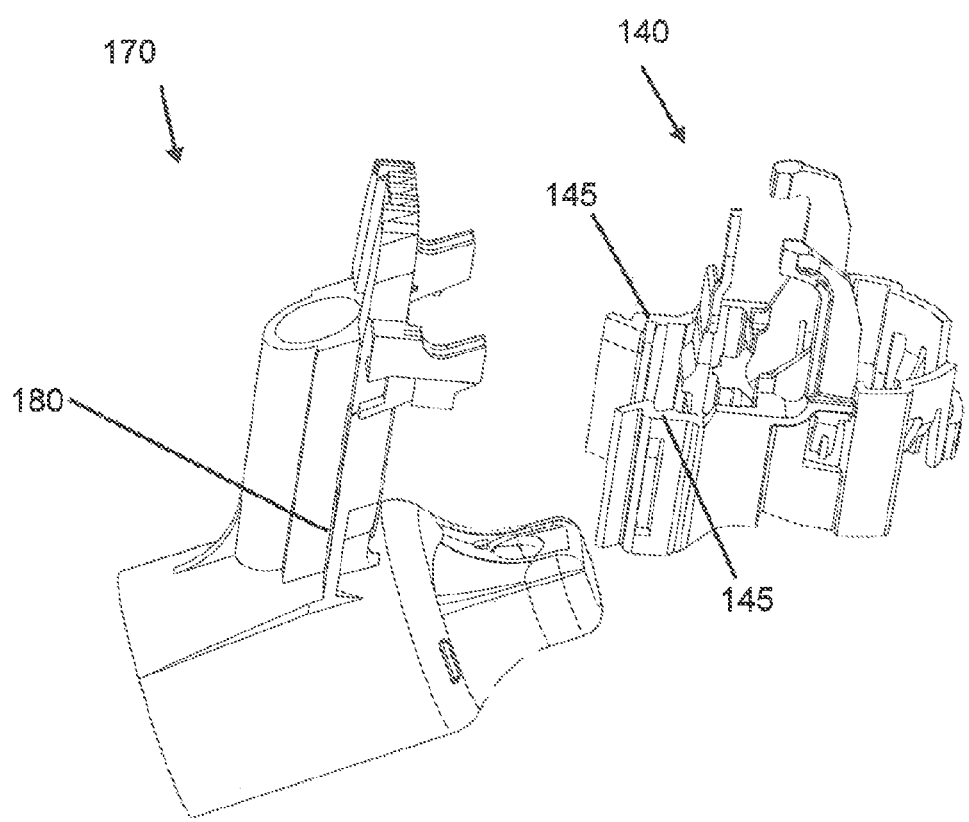
FIG. 6 is an exploded view of the Cradle and Manifold of the present invention.
Figure 7:
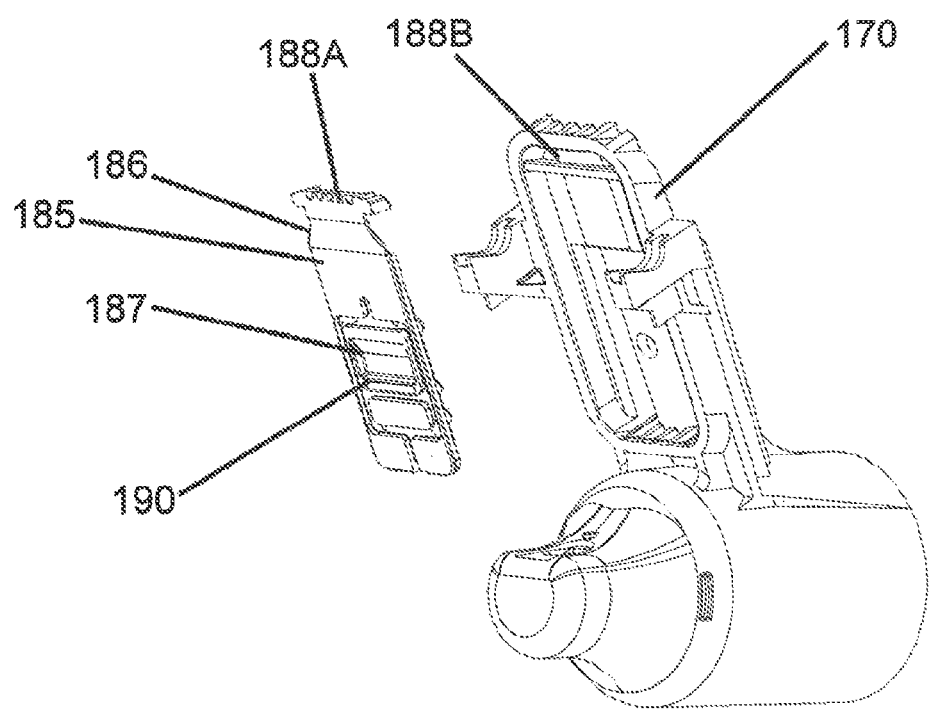
FIG. 7 is an exploded perspective view of the Manifold showing several of the breath actuation components.

2. Slideably Engages the Manifold 170;

Each of the first pair of arms 151 that extends away from the body of Cradle 140 contains a Slider Groove 145 (see FIG. 4) which engages with a corresponding mating part (the Cradle Rails 180) on Manifold 170 (see FIG. 6).

3. Provides One Part of the Latch to the Manifold Assembly;

Cradle Latch A 155, shown in FIG. 4, along with Trigger Shelf 190 (See FIG. 7) forms Cradle Latch Assembly (not shown) which detachably fixes Cradle 140 to Manifold 170. The second part of Cradle Latch Assembly is Trigger Shelf 190, which is positioned within Trigger Pocket 187 as shown in FIG. 5. Panel 185 is shown detached from Manifold 170. Panel 185 is normally positioned within Manifold 170 by positioning Attachment Bracket 188A within Panel Pocket 188B. Panel 185 through various gaskets and seals, not shown, can be biased at Flexible Location 186, and displaced into Manifold 170 by utilizing a venturi effect caused by the inspiration of air by the patient. If Panel 185 is biased inwards by the intake of breath of a patient on the inhaler, then Trigger Shelf 190 becomes disengaged from Cradle Latch A 155. This triggering action normally takes place after Spring Assembly has been compressed. The disengagement of the Cradle Latch Assembly then allows the Springs in the Spring Assembly to expand, forcing Cradle 140 downward which also forces Canister 167 downward causing a single dose of medicament to be discharged from Canister 167 through Canister Stem 168.

4. Provides One Part of Spring Assembly

Spring Assembly Latch A 157, as shown in FIG. 4 mates with a corresponding component on the Spring Assembly 240 which will be described below. The two components form Spring Assembly Latch 158, which is a key component of the lockout feature of the present invention and will be discussed below.

Figure 9:
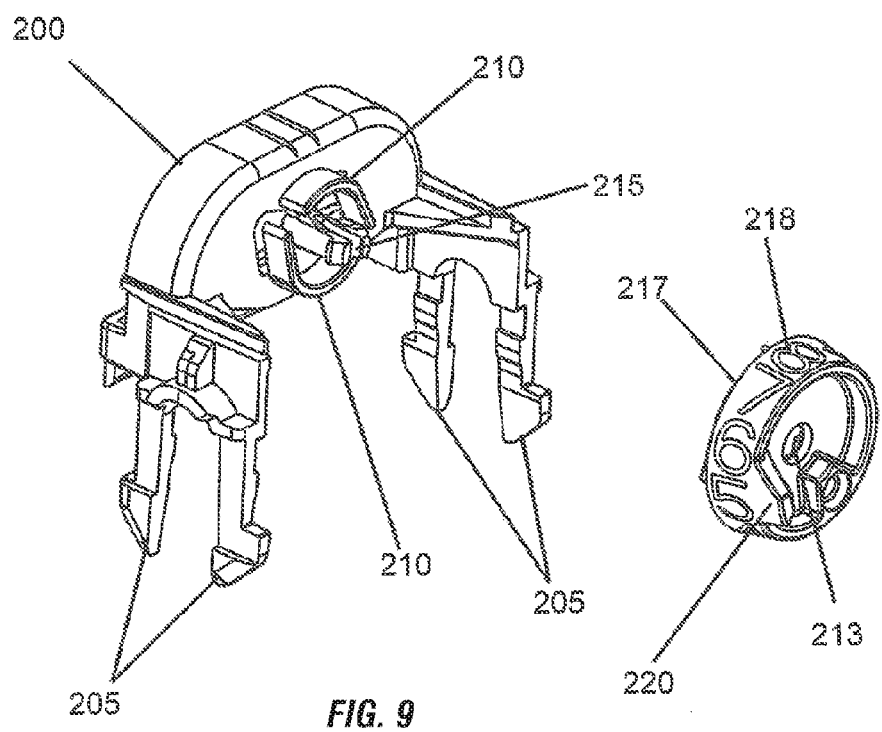
FIG. 9 is an exploded perspective view of the Cocking Lever Retainer and the Counter Wheel.

5. Actuates the Dose Counter Wheel;

Counter Actuation Rod 150 extends from Cradle 140 and contacts Counter Wheel 217, shown in FIG. 9. Each time the Cradle 140 (See FIG. 4) moves from its cocked position to its resting position, the Counter Actuation Arm 150 makes contact with notches on the periphery of Counter Wheel 217, causing it to rotate a predefined amount.

6. Provides Support for the Spring Assembly

Figure 13:
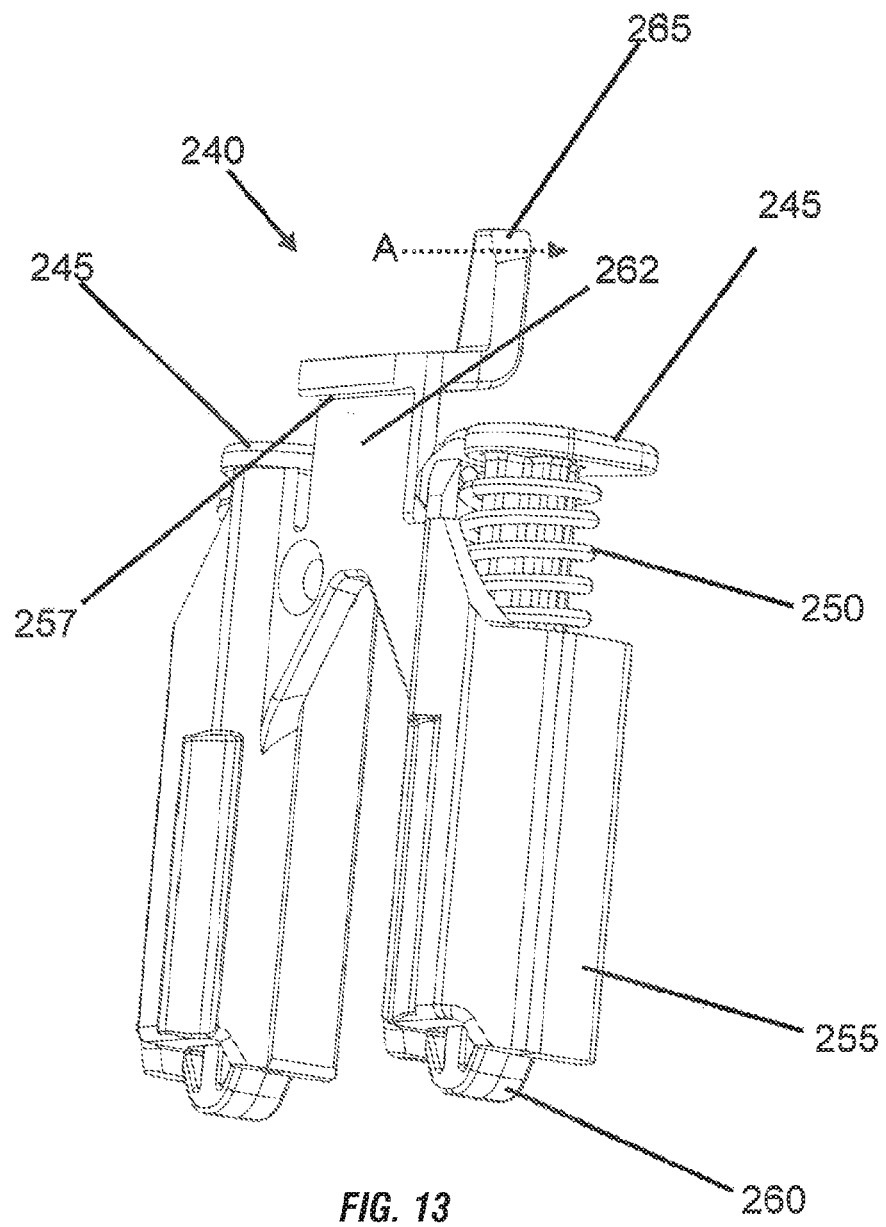
FIG. 13 is an alternate perspective view of Spring Assembly.
Figure 14:
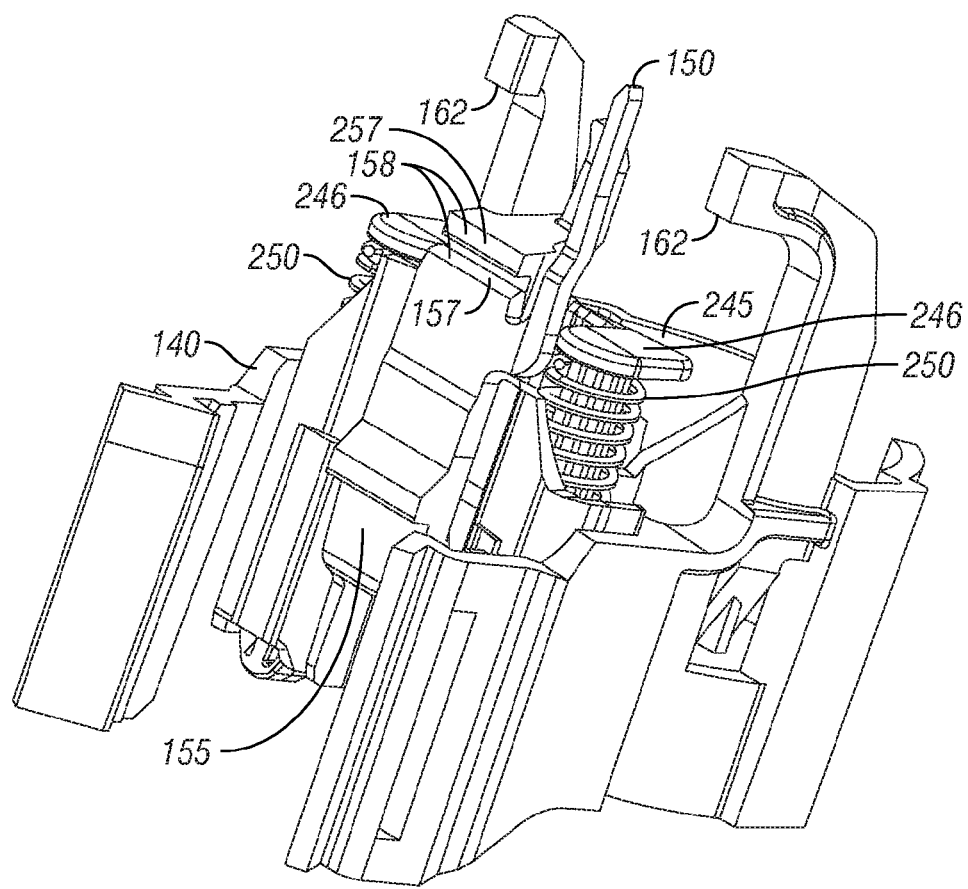
FIG. 14 is a perspective view of Spring Assembly disposed within the Cradle.

Spring Assembly 240 (shown alone in an expanded view in FIG. 11, and in a front and back view in FIGS. 12 and 13) is contained within Cradle 140 as shown in FIG. 14. As shown in FIG. 14, Spring Assembly Latch B 257 of Spring Assembly 240 is detachably engaged with Spring Assembly Latch A 157, which is part of Cradle 140. When Spring Assembly 240 is biased in the downward direction (as discussed below) the engaged Spring Assembly Latch 158 causes the downward force applied to the Spring Assembly to be transmitted to Cradle 140.

Figure 8A:
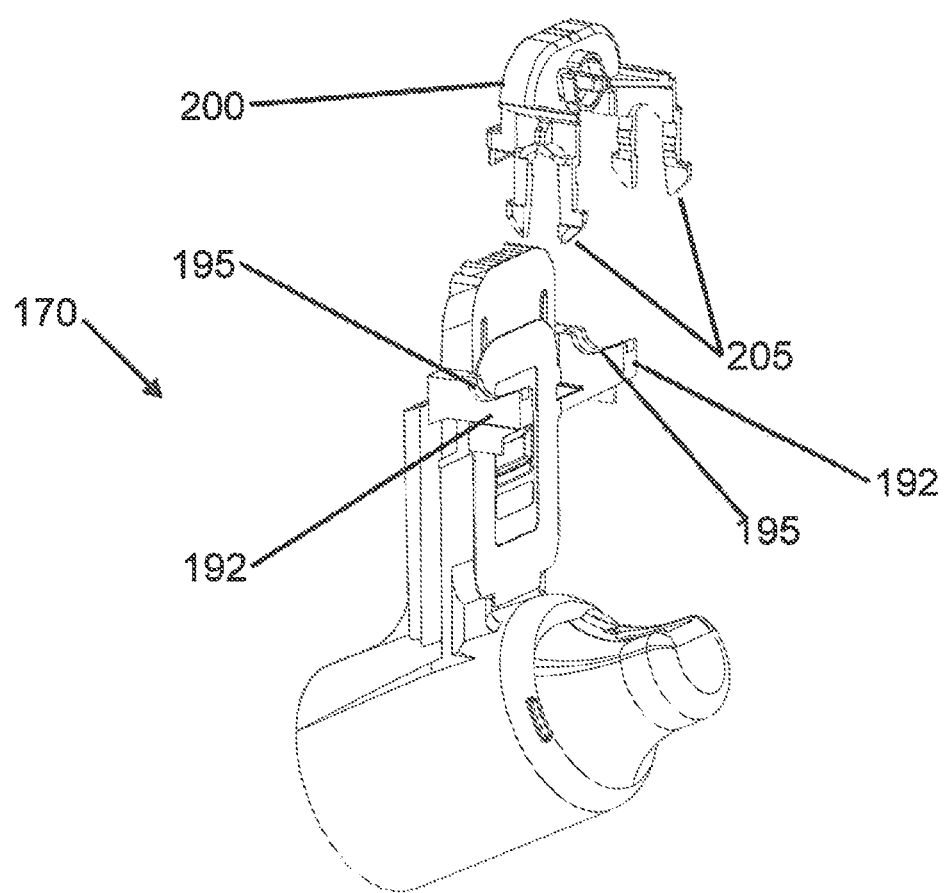
FIG. 8A is an exploded perspective view of the Manifold and the Cocking Lever Retainer.
Figure 8B:
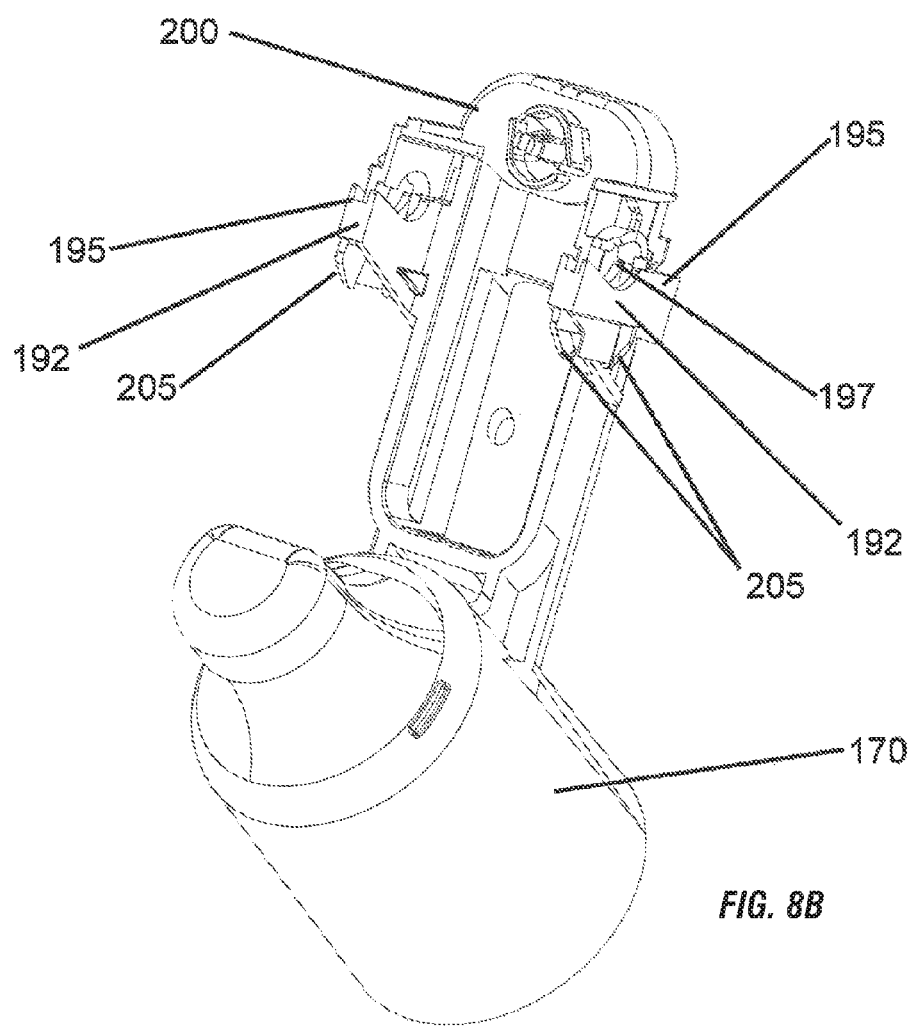
FIG. 8B shows Cocking Lever Retainer positioned on the Manifold.

FIG. 8A shows Cocking Lever Retainer 200 detached from Manifold Assembly 125. It is normally positioned on Manifold 170 as shown in FIG. 8B. Locking Tangs 205 are inserted into Slots 195. When Cocking Lever Retainer 200 is fully inserted into Manifold 170, there are two Cocking Lever Apertures 197 formed which are used to retain Cocking Lever 110 as will be discussed below.

FIG. 9 shows Cocking Lever Retainer 200 and Counter Wheel 217. Counter Wheel 217 fits over and is retained by Counter Wheel Axle 215. Counter Wheel Axle 215 is made up of two arms which are compressed. Counter Wheel 217 is then positioned such that the compressed arms of Counter Wheel Axle 215 are inserted through Mounting Hole 213 formed in the middle of Counter Wheel 217. Once Counter Wheel Axle 215 is fully inserted into and through Mounting Hole 213, the two arms are allowed to expand, which rotatably locks Counter Wheel 217 on Counter Wheel Axle 215. Counter Wheel 217 fits over Detent Arms 210 which are positioned to fit into Detent Teeth 230 as shown in FIG. 8. The interaction of Detent Arms 210 and Detent Teeth 230 permit Counter Wheel 217 to rotate in only one direction and in fixed increments determined by the spacing of Detent Teeth 230.

Figure 10:
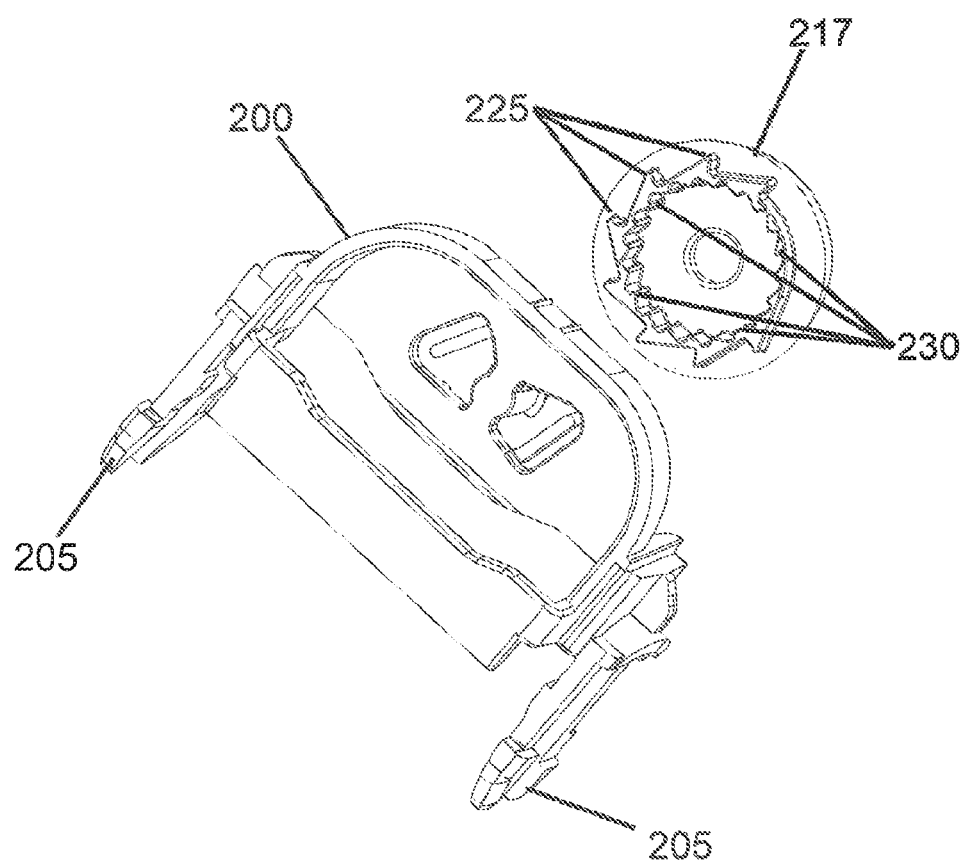
FIG. 10 is an alternative exploded perspective view of the Cocking Lever Retainer and the Counter Wheel.

Also shown in FIG. 10 are Rotation Actuation Teeth 225. These teeth are engaged by Counter Actuation Rod 150, located on Cradle 140, each time Cradle 140 is placed in its resting position. The spacing of Rotation Actuation Teeth 225 and Dose Numbers 218 are designed so that each movement of the Counter Actuation Rod 150 causes the next higher dosage number on Counter Wheel 217 to be visible in Dosage Counter Display Window 120.

Figure 11:
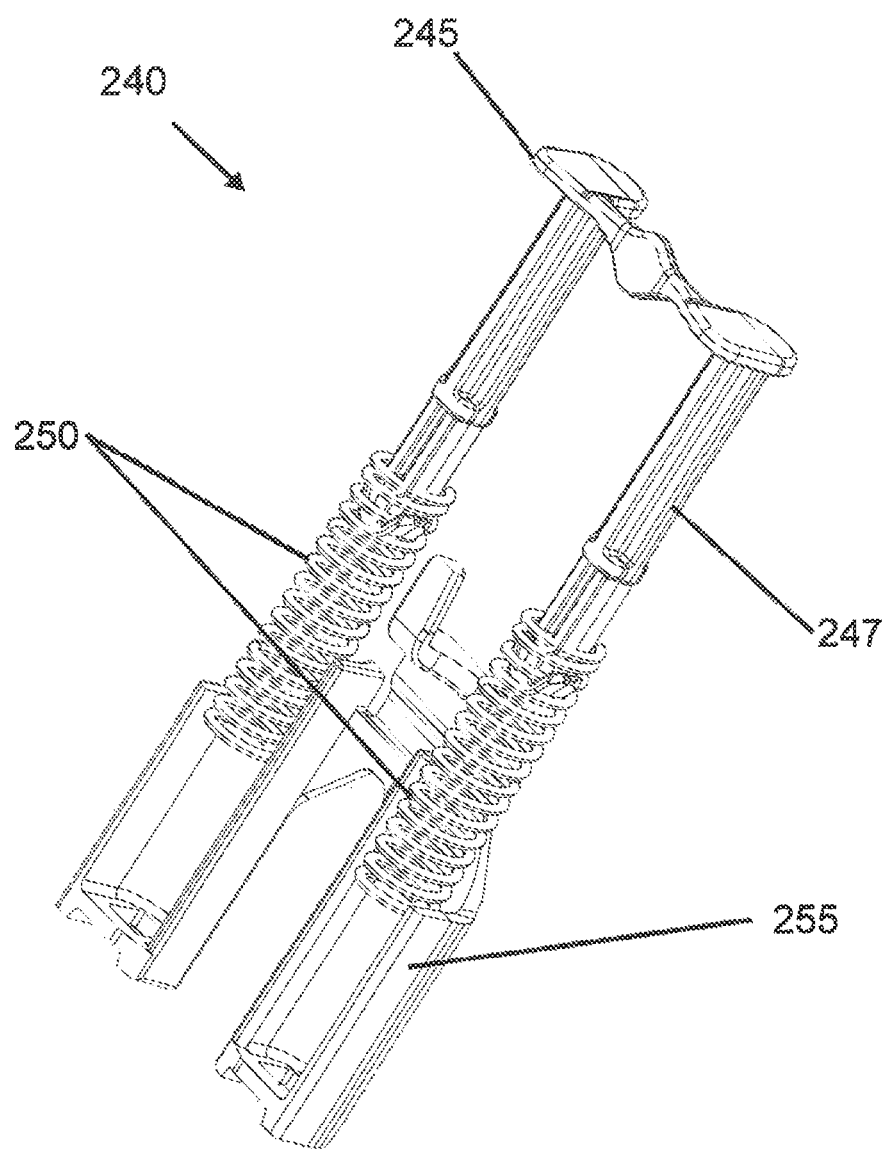
FIG. 11 is an exploded view of the Spring Assembly.
Figure 12:
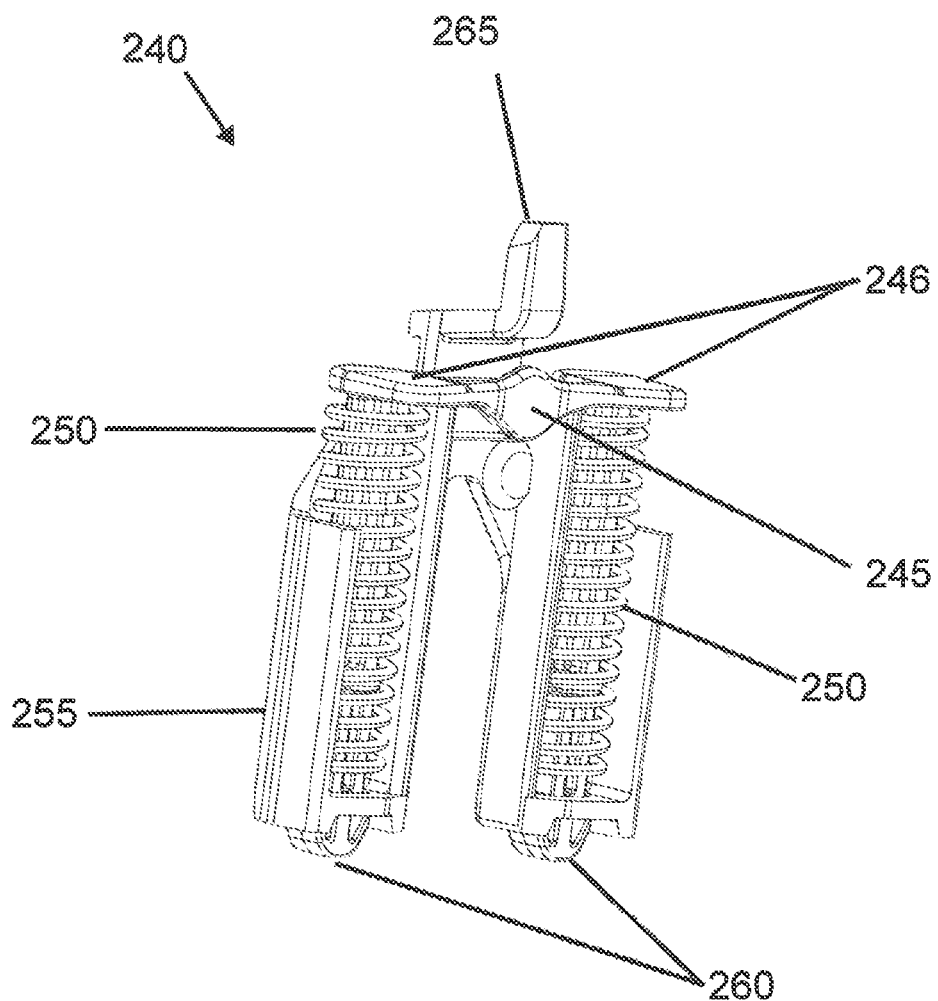
FIG. 12 is a perspective view of internal Spring Assembly.

Various views of Spring Assembly 240 are shown in FIGS. 11-13. The three main elements of Spring Assembly 240 are the Pusher 245, the Springs 250 and Spring Holder 255. An exploded view of Spring Assembly 240 is shown in FIG. 11.

FIG. 12 shows one view of the fully assembled Spring Assembly 240. One each of Springs 250 are placed over one each of Pusher Arms 247. This assembly is placed within Spring Holder 255 such that Pusher Retaining Tabs 260 are inserted through openings in the bottom of Spring Holder 255. Once place through these holes, Pusher Retaining Tabs 260 lock Pusher 247 within Spring Holder 255. The diameter of Springs 250 are smaller than the holes in the bottom of Spring Holder 255. Therefore, if Pusher 245 is biased downwards, Pusher Arms 247 are extended through the holes in the bottom of Spring Holder 255. This causes Springs 250 to be compressed between the lower portion of Spring Holder 255 and the top of Pusher 245.

FIG. 13 shows the opposite side of the view shown in FIG. 12. Dropout Tab 265, which is located on the Dropout Arm 262, is engaged by Dropout Cam 220 on Counter Wheel 217 (FIG. 9). When Dropout Tab 265 is biased by contact with Dropout Cam 220 it moves in the direction indicated by Arrow A. This causes Spring Assembly Latch A 157 to disengage from Spring Assembly Latch B 257.

When Spring Assembly Latch is engaged, any downward pressure on the Pusher 245 causes Springs 250 to compress and also transmits the downward pressure to Cradle 140. And because the Cradle Latch (Cradle Latch A 155 and Trigger Shelf 190) is usually engaged, Cradle 140 is prevented from making any significant downward motion. Thus the downward pressure on Pusher 245 results in the Cradle 140 being biased tightly against the Cradle Latch and also results in the compression of Springs 250.

However, when Spring Assembly Latch is disengaged, there can be no compression of Springs 250, and the whole Spring Assembly 240 is moved downward within Cradle 140, without imparting any downward force to Cradle 140. When there is no compression of Springs 250, there is no compression energy available to cause the downward motion of the Cradle 140 and the Canister 167 to overcome the forced needed to move the Canister Stem 168 into the Canister 167.

FIG. 14 shows in detail the Spring Assembly 240 positioned within Cradle 140 and with Spring Assembly Latch components (Spring Assembly Latch A 157 and Spring Assembly Latch B 257) in is an engaged, but slightly separated position in order to better view these two components. Normally Spring Assembly Latch A 157 and Spring Assembly Latch B 257 are in direct contact, unless Dropout Cam 220 has engaged Dropout Tab 265 to cause the two components to disengage and to potentially slide past each other.

Figure 15:
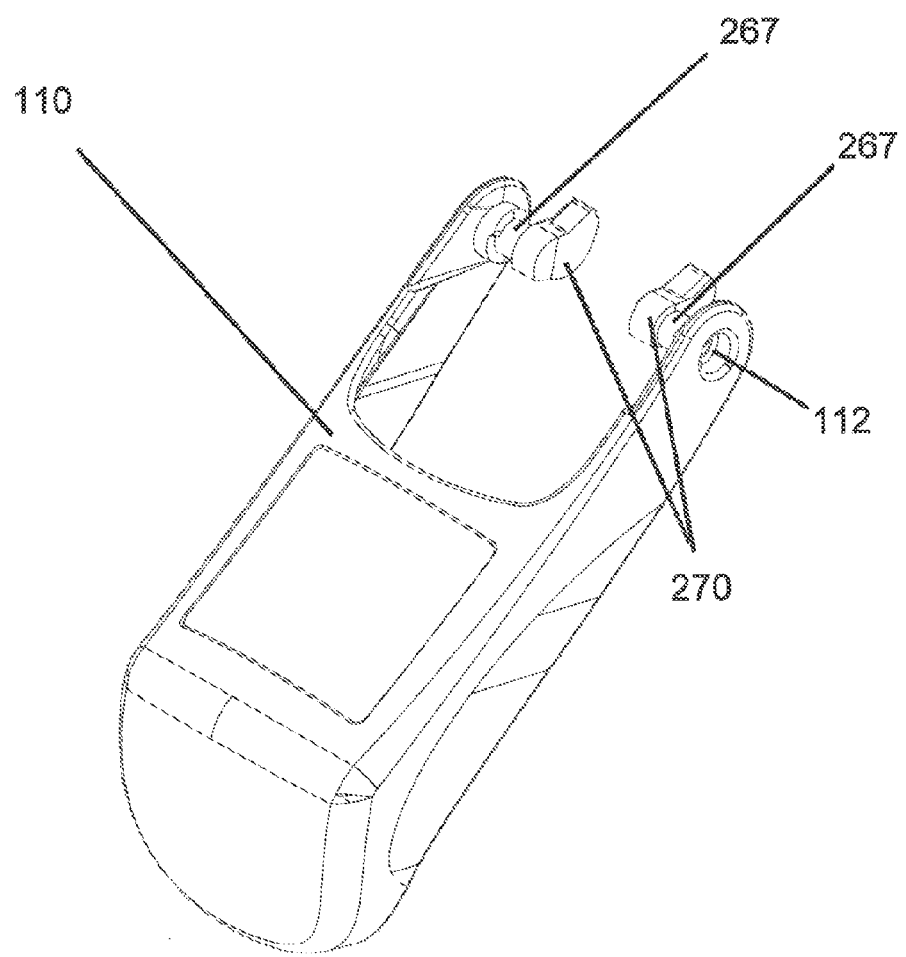
FIG. 15 is a perspective view of the Cocking Lever.
Figure 16:
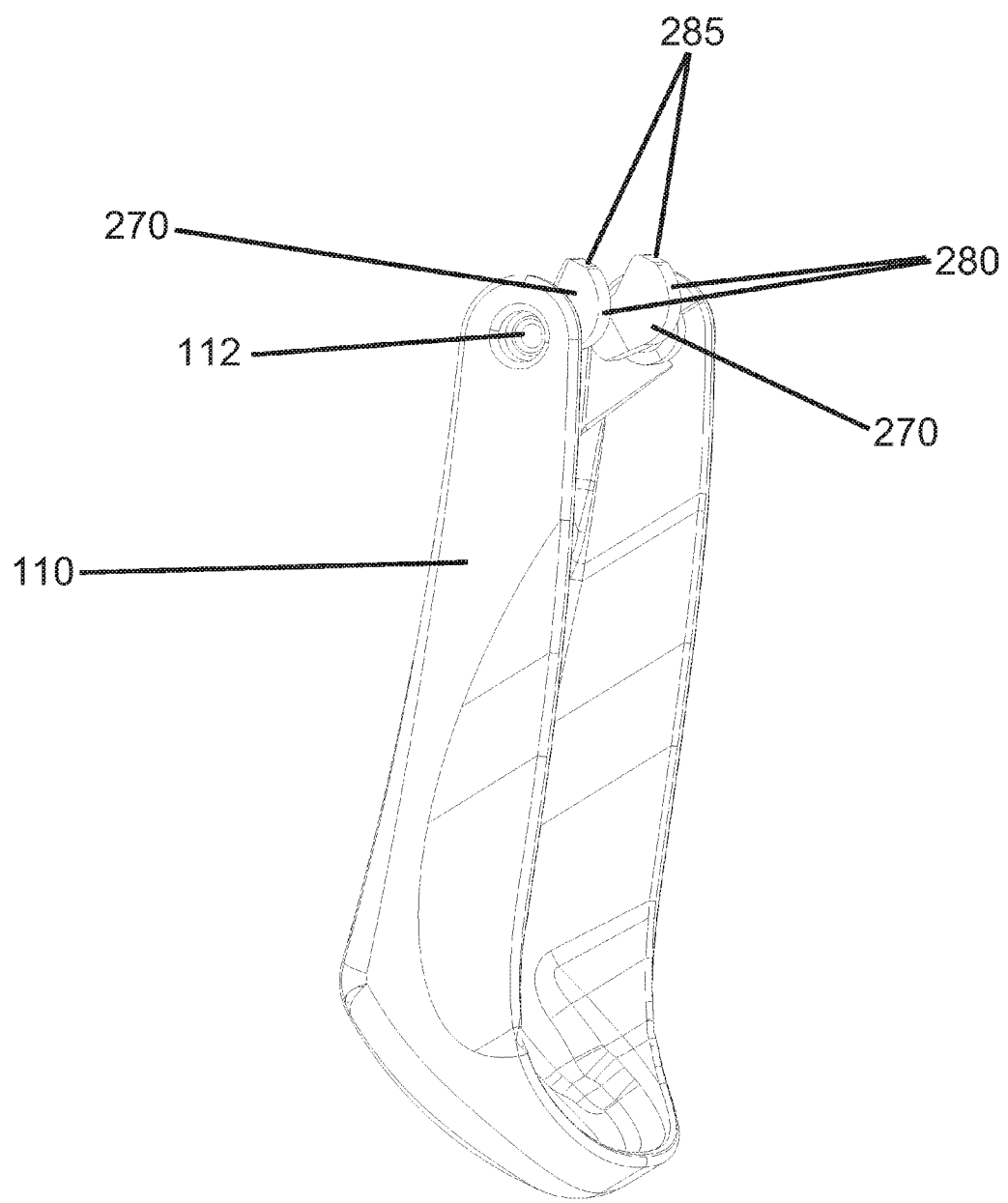
FIG. 16 is an alternate perspective view of Cocking Lever.

FIG. 15 shows Cocking Lever 110 with its Cams 270 and its Pivot Bearings 267 located at one end. Pivot Bearings 267 are pivotally retained within the Cocking Lever Apertures 197 formed by the Cocking Lever retainer and the Cocking Lever Support Brackets 192.

Figure 17:
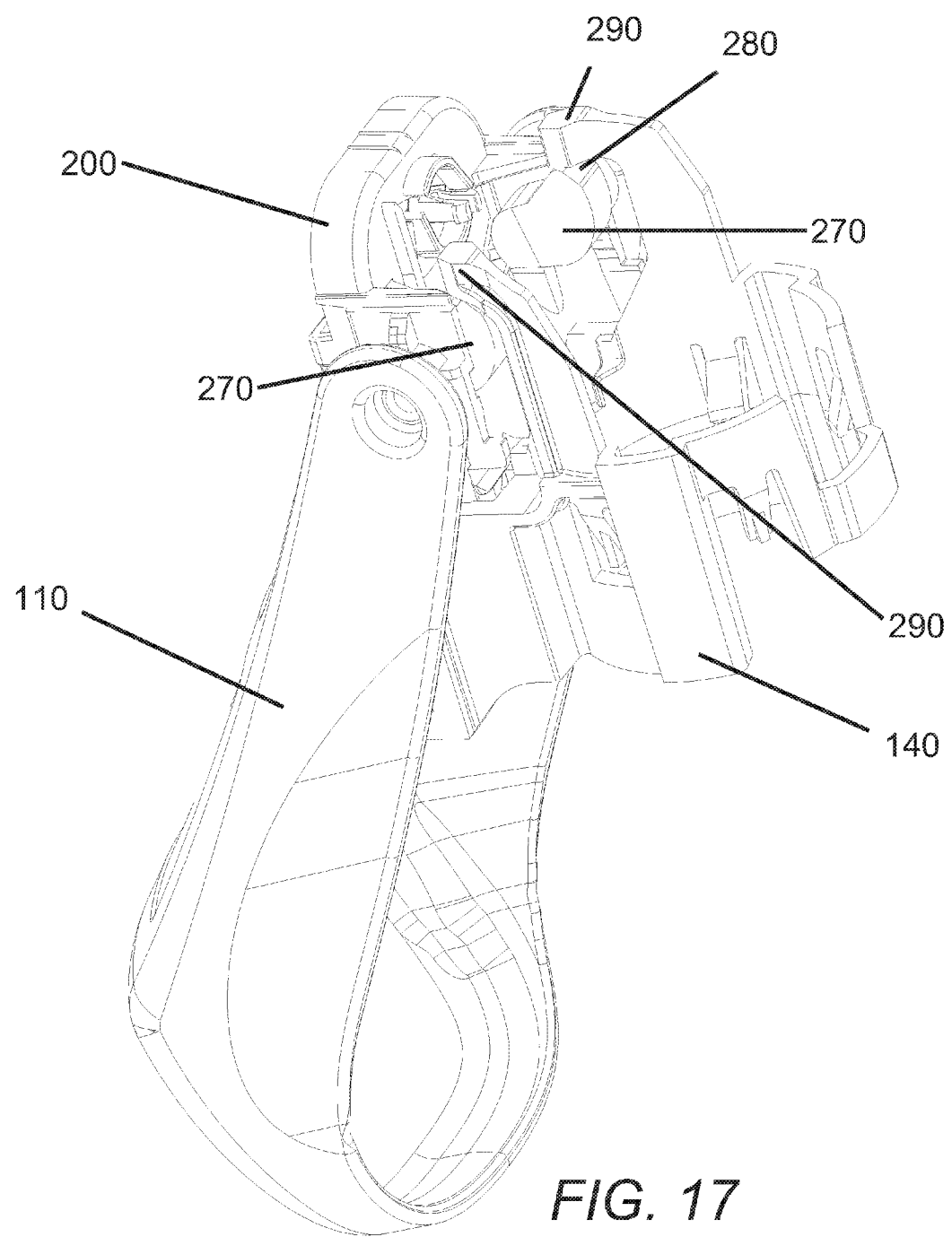
FIG. 17 is a perspective view of Cocking Lever, Cradle and Cocking Lever Retainer.

FIG. 17 shows Cocking Lever 110 is its closed or resting position. FIG. 17 also shows several of the components in the closed or resting positions. When Cocking Lever 110 is in the closed position, Cams 270 are oriented such that Reset Lobes 290 are located as shown in FIG. 17. In this position, Reset Lobes 290 are oriented upwards and directly in contact with Reset Cam Contact Surface 162. In this position, Cradle 140 is biased in its uppermost position.

During normal operation, as Cocking Lever 110 is rotated away from Mouthpiece 130, Cams 270 are rotated which brings Compression Lobes 280 into contact with Cam Contact Surface 246, which causes Pusher 245 to compress Springs 250.

When Cocking Lever 110 is rotated to its fully opened position (about 135 degrees), it brings the Stabilizing Surface 285 on Cam 270 in full contact with Cam Contact Surface 246. Because Stabilizing Surface 285 is flat, when it is in full contact with Cam Contact Surface 246, Cocking Lever 110 is stabilized it is fully open position which holds Springs 250 in a compressed state.

Typically, the next step is to trigger Cradle Latch Assembly, which disengages Cradle Latch A 155 from Trigger Shelf 190. Cradle 140 is then biased by the expansion of Springs 250. The force of the expansion of compressed Springs 250 is sufficient to overcome the force on Canister Stem which biases Canister Stem 168 into Canister 167 to cause delivery of a metered dose of medicament.

After the delivery, Cocking Lever 110 is rotated back to the closed position which causes Reset Lobe 290 to be rotated against Reset Arm Contact Surface 162 which returns Cradle 140 back to its normal position. When Cradle 140 is in its uppermost position, Cradle Latch Assembly reengages, causing Cradle 140 to be fixedly attached to Manifold 170.

Figure 18:
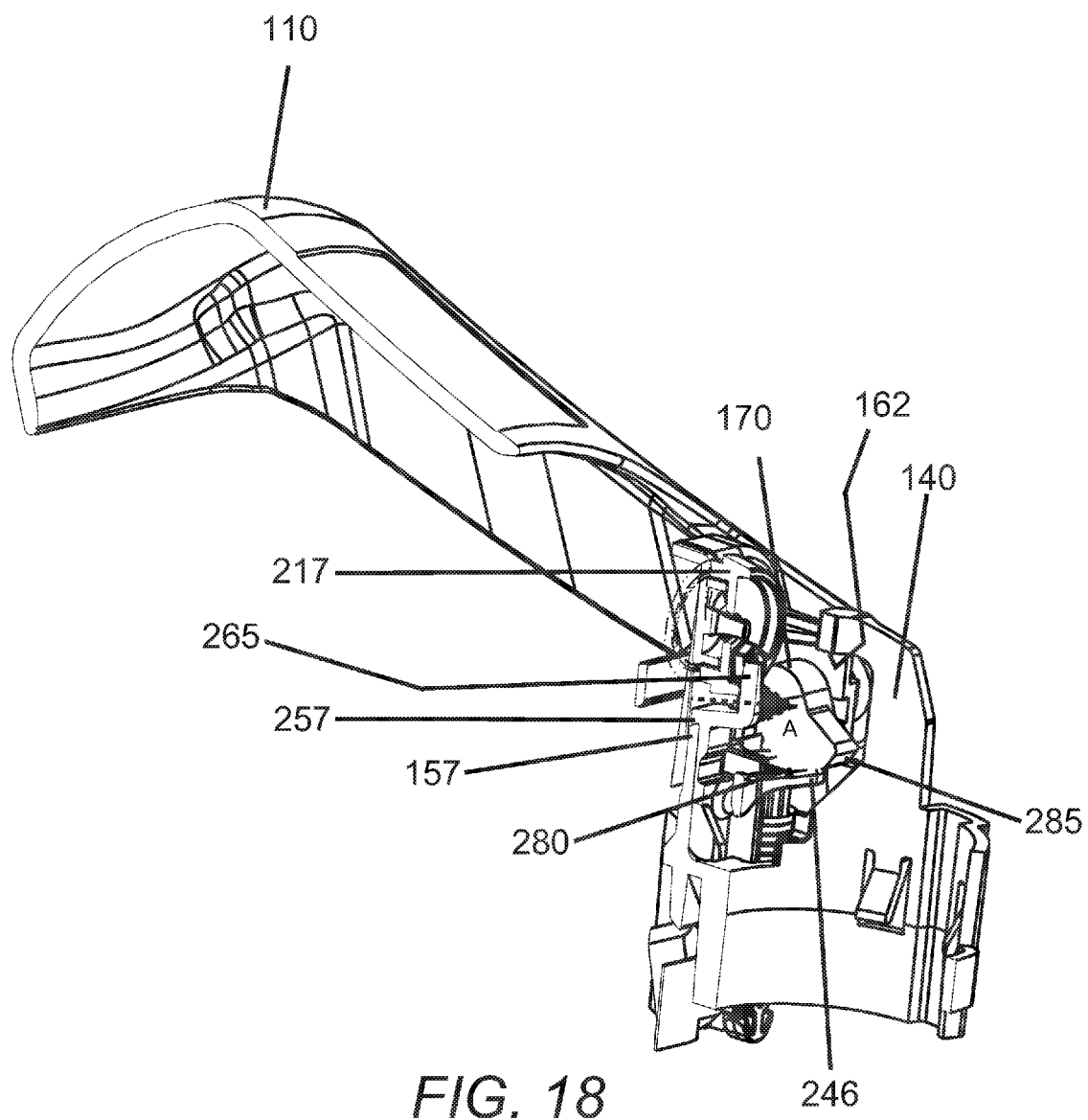
FIG. 18 is a cutaway view showing Cocking Lever in a partially elevated position.

FIG. 18 shows a cutaway view of the Inhaler 100 with the Cocking Lever 110 in a partially elevated position. Cam 270 is shown oriented such that Compression Lobe 280 is in contact with Cam Contact Surface 246. In this configuration Pusher 245 is biased in a downward direction which results in Springs 250 being partially compressed.

FIG. 18 also shows Spring Assembly Latch B 257 engaged with Spring Assembly Latch A 157. If Cocking Lever 110 were to be raised further, Stabilizing Surface 285 would be rotated so that it comes in contact with Cam Contact Surface 246 and be held in a stabilized position.

The present invention may be embodied in other specific forms without departing from its spirit or essential characteristics. The described embodiments are to be considered in all respects only as illustrative and not restrictive. Therefore, the scope of the invention is not limited to the exemplary embodiment described above. All changes or modifications within the meaning and range of equivalents are intended to be embraced herein.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

The presence of broadening words and phrases such as "one or more," "at least," "but not limited to" or other like phrases in some instances shall not be read to mean that the narrower case is intended or required in instances where such broadening phrases may be absent.

As used in this application, the articles "a" and "an" refer to one or more than one (i.e., to at least one) of the grammatical objects of the article. By way of example, "an element" means one element or more than one element.

What is claimed it:

1. A metered dose inhaler comprising:
   (a) a pressurized canister containing a medicament formulation, said canister further comprising a metering valve having a spring loaded valve stem;
   (b) an inhaler body;
   (c) a cradle which fixedly holds said canister, and which is slideably engaged with said inhaler body;
      said cradle comprising a cradle latch, said cradle latch having:
         (i) an engaged configuration in which said cradle adopts a first position, wherein its movement is restricted along said inhaler body; and
         (ii) a disengaged configuration in which said cradle adopts a second position, wherein its movement is not restricted along said inhaler body;
      wherein said cradle further comprises a reset arm and an actuation arm;
   (d) a compression assembly comprising a compression assembly latch that detachably affixes said compression assembly to said cradle; said compression assembly latch having:
      (i) an engaged configuration in which said compression assembly is fixedly attached to said cradle; and
      (ii) a disengaged configuration in which said compression assembly is slideably engaged with said cradle;
   (e) a dose counter wheel adapted to be detentably rotatable in one direction;
      wherein said dose counter wheel comprises a dropout cam; and
   (f) a lobed cam positioned between said cradle reset arm and said compression assembly; such that:
      (i) when said lobed cam is oriented in a first position, the cam lobe is biased against said reset arm and urges said cradle into said first position; and (ii) when said lobed cam is oriented in a second position said cam lobe is biased against said compression assembly, which causes mechanical energy to be stored in said compression assembly when said cradle latch and said compression assembly latch are both in the engaged positions;

wherein said inhaler is configured such that said actuation arm engages with said dose counter wheel and causes said dose counter wheel to incrementally rotate each time said cradle moves from said second position to said first position; said dose counter wheel is adapted to display a different dose indicia each time said dose counter wheel is incrementally rotated; and said dropout cam is adapted to cause said compression assembly latch to disengage after a predetermined number of incremental rotations; and whereby after the predetermined number of incremental rotations have passed, there is no physical blocking or interference of any of the foregoing moving parts of the inhaler, such that said compression assembly can no longer be compressed, thereby disabling the metered dose inhaler and preventing further discharge of said medicament formulation.

2. A metered dose inhaler as described in claim 1 wherein said cradle latch is manually disengaged.

3. A metered dose inhaler as described in claim 1 wherein disengagement of said cradle latch is breath-actuated.

4. A metered dose inhaler as described in claim 1 further comprising a cover which rotates within said inhaler body, said cover further comprising said lobed cam.

5. A metered dose inhaler as described in claim 1 wherein said compression assembly comprises one or more springs.

6. A metered dose inhaler as described in claim 1 wherein said compression assembly latch comprises a first and second latching member, said first latching member fixedly attached to said compression assembly and said second latching member fixedly attached to said cradle, wherein at least one said latching members can be directly or indirectly physically displaced by said dropout cam so that said compression assembly and said cradle are not fixedly attached to each other.

7. A metered dose inhaler as described in claim 1 wherein said dose counter wheel has numbers on the periphery of said dose counter wheel; said inhaler adapted to indicate a specific number as the number of interest.

8. A metered dose inhaler as described in claim 7 wherein said inhaler is adapted to display either the number of activations that have occurred or the number of activations remaining.

* * * * *